United States Patent [19]

Fruehauf

[11] Patent Number: 5,543,139
[45] Date of Patent: Aug. 6, 1996

[54] 5.5 KD TNF DEGRADATION PRODUCT

[76] Inventor: John P. Fruehauf, 18828 Teton Cir., Fountain Valley, Calif. 92708

[21] Appl. No.: 259,137

[22] Filed: Jun. 13, 1994

Related U.S. Application Data

[63] Continuation of Ser. No. 902,309, Jun. 22, 1992, abandoned.

[51] Int. Cl.$^6$ .............................. A61K 38/19; C07K 2/00; C07K 14/00
[52] U.S. Cl. ...................... 424/85.1; 424/520; 530/300; 530/350; 530/351; 530/402; 530/407
[58] Field of Search .................................. 424/85.1, 52.0; 574/2, 12; 530/357, 350, 300, 402, 407

[56] References Cited

PUBLICATIONS

Wantanabe et al., *Immunpharm. Immunotox.* (1988) 10(1):109–116.
Aggarwal et al., *J. Biol. Chem.* (1986) 261(29):13652–13656.
Liddil et al., *Cancer Res.* (1989) 49:2722–2728.
Ohsawa et al., *J. Biochem.* (1988) 103:730–734.
Fruehauf et al., *J. Immunotherapy*(1991) 10:165–173.
Freuhauf et al., *J. Natl. Cancer Inst.* (1990) 82(14):1206–1209.
Sugarman et al., *Cancer Res.* (1987) 47:780–786.
Lichtenstein et al., *Cancer Res.* (1990) 50:7364–7370.
Hudziak et al., *Mol. Cell. Biol.* (1989) 9(3):1165–1172.
Smith et al., 1987. J. Biol. Chem (262) 15: 6951–6954.
Kunitani et al., 1988 J. Chromatog. 443: 205–220.

*Primary Examiner*—Garnette D. Draper
*Assistant Examiner*—K. Cochrane Carlson
*Attorney, Agent, or Firm*—Morrison & Foerster

[57] ABSTRACT

A particular TNF degradation product is effective as a cytotoxin with respect both to TNF-sensitive and TNF-resistant tumor cells. Pharmaceutical compositions containing this degradation product are thus useful in treating tumors which are otherwise resistant to TNF. In addition, TNF resistance can be measured as a function of the expression of EGF receptors in tumor cells.

2 Claims, 10 Drawing Sheets

FIG. 5A   WT
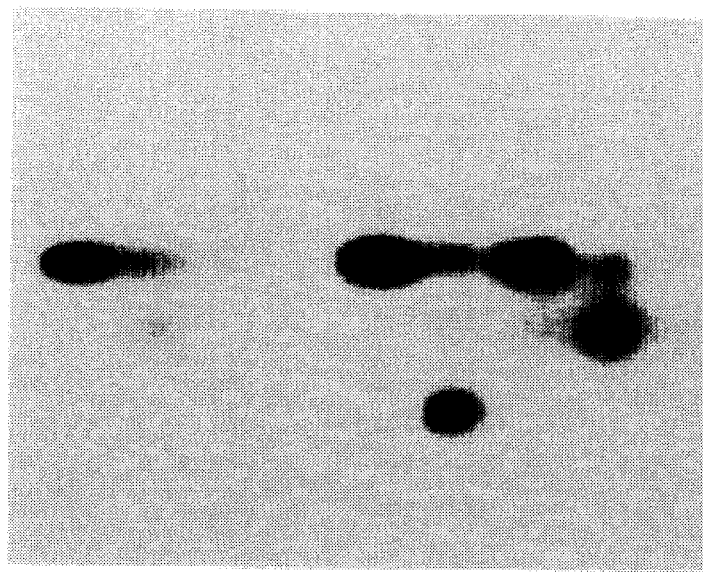
FIG. 5B   LNCaP
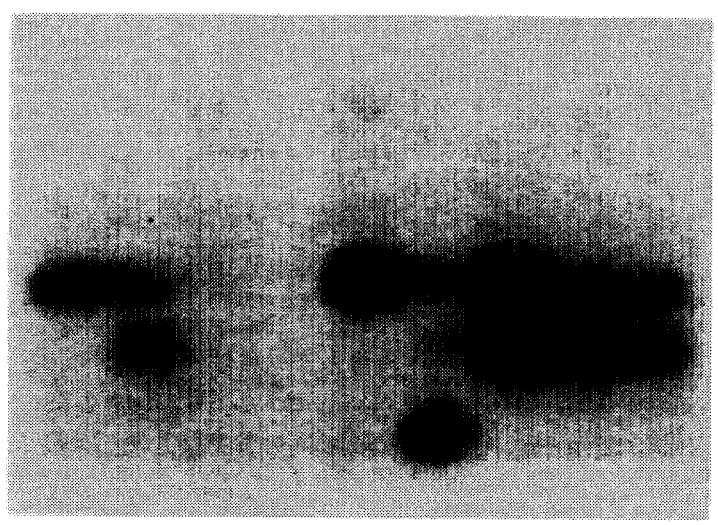

5.5 KD TNF DEGRADATION PRODUCT

This invention was made with the support of the National Cancer Institute, a part of the National Institutes of Health. The United States government has certain rights in this invention.

This application is a continuation of application Ser. No. 07/902,309, filed Jun. 22, 1992, now abandoned.

FIELD OF THE INVENTION

The invention relates to methods to control tumor cell proliferation and to TNF cytotoxicity against tumor cells. In particular, the invention concerns the use of a TNF degradation product to exert a toxic effect on tumor cells otherwise resistant to TNF.

BACKGROUND ART

Although tumor necrosis factor (TNF) exhibits significant antitumor activity toward some cell cancer lines in vitro, it has not been notably successful in the clinic. This is partly due to the negative side effects of the required levels of TNF in vivo and, perhaps more importantly, many tumors are, or become, resistant to TNF treatment.

It is believed that TNF is internalized through interaction with a TNF receptor, and a number of mechanisms have been postulated for the action of the internalized TNF. Agents that block TNF internalization or lysosomal enzyme function protect cells from TNF-mediated killing (Watanabe, N., et al., *Immunopharm Immunotox* (1988) 10:109–196; Aggarwal, B. B., *J Biol Chem* (1986) 261:13652–13656; Liddel, J. D., et al., *Cancer Res* (1989) 49:2717–2718). It has been shown that TNF-sensitive murine L-929 cells release a degradation product into the media which disrupts lysosomes; TNF-resistant L-929 internalize TNF but do not produce a degradation product (Ohsawa, F., et al., *J Biochem* (1988) 103:730–734).

In a previous study, the inventors herein reported that MCF-7 cells that were sensitive to TNF internalized TNF and degraded it to a 15 kd species and appeared to recycle the receptor. On the other hand, MCF-7 cells that were resistant to TNF produced multiple lower molecular weight TNF products and showed decreased binding over time consistent with lysosomal degradation of the receptor TNF complex (Fruehauf, J. P., et al., *J Immunotherapy* (1991) 10:165–173, incorporated herein by reference). This pattern was also shown in prostate cell lines (Freuhauf, J. P., et al., *J Nat Cancer Inst* (1990) 82:12–16–1207).

It has now been found that a fraction of conditioned media from TNF-treated TNF-sensitive cells is cytotoxic both to TNF-sensitive and TNF-resistant tumor cells.

Previous reports have suggested that TNF resistance may be related to growth factor receptor expression, including those of Sugarman, B. J., et al., *Cancer Res* (1987) 47:780–786; Lichtenstein, A., et al., *Cancer Res* (1990) 7364–7370; Hudziak, R. M., et al., *Mol Cell Biol* (1989) 9:1165–1162. It has now also been shown that EGF receptor expression correlates with TNF resistance.

DISCLOSURE OF THE INVENTION

The invention provides a TNF degradation product available from the conditioned media of TNF-sensitive cells which is cytotoxic both to TNF-resistant and TNF-sensitive tumors. This degradation product and its pharmaceutical compositions thus provide a means for treating previously resistant tumors.

Thus, in one aspect, the invention is directed to a method to treat tumor cells, which method comprises contacting the cells with a TNF degradation product obtainable from conditioned media of TNF-sensitive cells.

In another aspect, the invention is directed to pharmaceutical compositions containing this degradation product.

It has also been shown that TNF resistance can be assessed by the level of expression of EGF receptor. Accordingly, in still another aspect the invention is directed to a method to assess TNF resistance in a tumor cell sample, which method comprises assessing the level of expression of EGF receptor in the tested cells as compared to control TNF-sensitive tumor cells.

BRIEF DESCRIPTION OF THE DRAWINGS

FIGS. 5A and 5B shows photocopies of SDS-PAGE audiograms of labeled conditioned media that have been fractionated by hydrophobic interaction chromatography.

MODES OF CARRYING OUT THE INVENTION

Figure 1A:
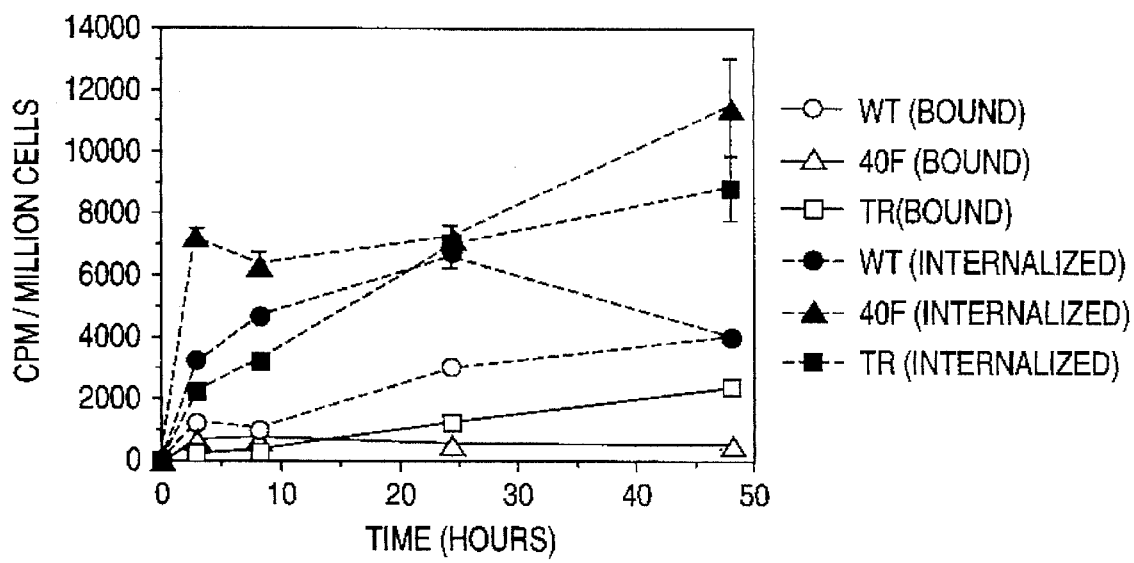
FIGS. 1A and 1B show the binding and internalization of labeled TNF to various cell lines.

The invention provides a degradation product of TNF that is useful in treating both TNF-resistant and TNF-sensitive tumor cells. The degradation product is a 5.5 kd fragment of TNF or a multimer thereof, and is obtainable by hydrophobic interaction chromatography of TNF-conditioned media from TNF-sensitive cells by the process described herein.

The purified degradation product can be used to treat tumor cells in vitro or in vivo. For in vivo use, the degradation product may be formulated into pharmaceutical compositions suitable for administration to a whole organism. Such pharmaceutical compositions for administration of active compounds are generally those known in the art and may be found in, for example, *Remington's Pharmaceutical Sciences*, latest edition, Mack Publishing Company, Easton, Pa. These formulations typically include formulations for injection by intravenous, intramuscular, intraperitoneal or subcutaneous routes, or for transmucosal or transdermal administration. Oral formulations may also be used.

The 5.5 kd degradation product may be administered as a pharmaceutically acceptable salt, depending on the pH-status of the medium of its preparation and/or administration. The dosage level is determinable using standard optimization procedures known in medical and veterinary practice, and depends on the nature of the formulation, the route of administration, the severity of the tumor burden of the subject, and the judgement of the relevant practitioner.

In the illustrations used below, several cell lines were used.

TNF-sensitive cell lines:
WT (wild-type MCF-7 cell line); and
LNCaP (a prostate cancer line).
TNF-resistant cell lines:
40F (a doxorubicin-resistant MCF-7 cell line);
TR (a resistant MCF-7 cell line); and
PC3 (a TNF-resistant prostate cell line).

To prepare the degradation product, conditioned media are prepared with $10^7$ WT, 40F or LNCaP cells incubated in IMEM+5% FBS medium containing 10 ng/ml TNF under standard culture conditions for 48 hours. Media containing native TNF and its conditioned products are collected and concentrated on a dialysis or membrane filter system such as a Micro-Pro-DiCon dialysis system (Biomolecular Dynamics, Beaverton, Oreg.) using a PA-10 ProDiMembrane (10 kd cutoff) for unlabeled TNF-conditioned media, or, for $^{125}$I-TNF-conditioned media, with a Centiprep-10 filtration device (Amicon, Danvers, MA).

The conditioned media are tested for activity in an assay system using MTT (3-(4,5-dimethylthiazol-2-yl) -2,5-diphenyltetrazolium bromide dissolved at 2 mg/ml in phosphate-buffered saline. In the assay, cells sensitive to TNF are carried in drug-free media for a minimum of 4 passages, then harvested by trypsinization, suspended in fresh media, plated at 1000 cells/well in 96-well microtiter plates (Costar) and reincubated overnight to allow for attachment. After addition of TNF-containing media, the cells are incubated for 4 days of continuous drug exposure. Cells intended for the MTT assay are pulsed with MTT, incubated for 3 hours, centrifuged at 2000×g, and the media are decanted. Dimethyl sulfoxide (0.12 ml) is then added to each well, and the plates shaken for 30 minutes. The O.D. at 570 nm is then read on a microplate reader. The average of 3 repetitions is used as the result. The assay is described by Forthoff, J. P., et al., *J Nat Cancer Inst* (1990) 81:1206–1209, and the statistical treatment of the data is described by Chau, T. C., et al., in "Advances in Enzyme Regulation"(1982), 22:27–55, Oxford: Pergamon Press.

The conditioned media containing TNF activity is subjected to hydrophobic interaction chromatography according to the method of Kunitani, M. G, et al., *J Chromatog* (1988) 443:205–220. Briefly, a gradient system employing two mobile phases is utilized with mobile A consisting of 1M ammonium sulfate and 0.1M sodium phosphate, pH 9.0; mobile B consisting of 0.1M sodium phosphate and 70% ethylene glycol, pH 9.0. A linear gradient of 0–100% B in 65 minutes at a flow rate of 0.5 ml/min at ambient temperature is employed, and the elution is monitored at 214 nm. Labeled TNF is detected using a Flow 1 beta detector (Radiomatic). Fractions containing TNF species are evaluated for molecular weight on 17–27% SDS-PAGE. TNF is also determined using an ELISA kit (New England Nuclear). The elution patterns obtained are shown in FIG. 4 (A–E) as further described hereinbelow.

The following examples are intended to illustrate but not to limit the invention.

Materials and Methods

Chemicals and Drugs

Improved minimum essential media (IMEM) (Gibco) supplemented with 2 mM L-glutamine, 2 mg/liter proline, 50 μg/ml gentamicin and 5% fetal bovine serum (Gibco, Grand Island, N.Y.) (IMEM+) was used for all MCF-7 cell line experiments, while RPMI 1640, supplemented with 10% fetal calf serum and PSN antibiotic mixture (Gibco), was used for experiments with prostate cell lines (PC3 and LNCaP). Doxorubicin hydrochloride (NSC 123127) was provided by the Drug Development Branch. Recombinant human tumor necrosis factor-alpha (Cetus) had 15,000 units of activity per mg material. MTT (3-(4,5-dimethylthiazol-2-yl)-2,5-diphenyltetrazolium bromide) (Sigma) was dissolved at 2 mg/ml in phosphate-buffered saline (Gibco). Dimethyl sulfoxide ($Me_2SO$) (Sigma) was 99% pure, reagent grade. $^{125}$I-TNF (NEN) had a specific activity of 45 μCi/μg. 40-mer oligonucleotide probes for mdr-1, TGF-β1, c-erbB2/neu, and human EGF-receptor (Oncogene Science, Inc.) were phosphorylated by the T4-polynucleotide kinase method (Lofstrand Labs Limited).

Cell Culture and Cytotoxicity Assays

MCF-7 cell lines were maintained as monolayer cultures in IMEM+under standard culture conditions at 37° C. in a humidified 5% $CO_2$ atmosphere. 40-fold doxorubicin-resistant MCF-7 cells (40F), kindly provided by Dr. Kenneth H. Cowan, were selected for doxorubicin resistance through chronic exposure to progressively increasing doxorubicin concentrations. The doxorubicin resistant phenotype was stable in culture for at least two months in drug-free media. PC3 and LNCaP cell lines were obtained from American Type Culture Collection (Rockville, Md.), and grown as adherent monolayers in RPMI 1640 supplemented with glutamine, gentamicin and 10% fetal calf serum under standard culture conditions.

TNF-Resistant Cells

TNF-resistant MCF-7 cells were selected by growing MCF-7 WT cells in TNF containing medium, with increasing doses applied every 4 days for 5 passages. The TNF-resistant phenotype of these cells was stable in drug free media for more than 4 months. These cells were designated as TR.

Scatchard Binding $2\times10^6$ cells per well were plated in 6 well plates (Costar), incubated overnight, and treated with increasing concentrations of $^{125}$I-TNF in the absence (total binding), or presence of a 100-fold excess of unlabeled TNF (nonspecific binding). The plates were incubated for 2 hours at 4° C., rinsed 3 times with Hanks balanced salt solution, and the cells harvested with 0.3 ml 10% sodium dodecyl sulfate. The radioactivity of the well contents was determined on a liquid scintillation counter (2000CA Tri-Carb, Packard). Specific binding of TNF, receptor numbers and dissociation constants (Kd) were determined by Scatchard analysis with the Ligand-PC program. (37)

TNF Binding, Internalization and Degradation $^{125}$I-TNF binding, internalization, and degradation were determined as previously described. (19)

Receptor Cross-Linking

Cells were harvested with Versene 1:5000 (Gibco), washed in PBS and resuspended in growth media at $2\times10^7$ cells in 200 μl media containing 8 nM $^{125}$I-TNF with or without 800 nM unlabelled TNF, mixed for 2 hours on ice, washed twice with RPMI, mixed with 1.25 ml of 1 mM $BS^3$ cross-linking buffer (PBS+1 mM MgCL, pH 8.3) for 30 minutes, washed once with PBS containing 0.1% sodium azide and the cross-linked receptors extracted over 30 minutes on ice with 200 μl of extraction solution containing 300 mM NaCl, 50 mM Tris, pH 7.5, 1% Triton X-100 (Sigma) and 1 mM PMSF (Sigma). The extraction mixture was centrifuged at 9,000 ×g for 8 minutes and the supernatant was collected, mixed with gel loading buffer and run on either 4–20% or 10–20% gradient SDS-PAGE mini-gels (Integrated Separation Systems, Natick, MA) with appropriate molecular weight standards. Gels were dried and exposed to Kodak XAR-2 film at −70° C. for 7 days.

Northern Analysis

Northern analysis of RNA from TNF-sensitive and -resistant cells was performed by standard techniques. For RNA extraction, $10^8$ cells were harvested by trypsinization, vortexed with 50% guanidine isothiocyanate buffer, layered over 3.5 ml CsCl, ultracentrifuged overnight, the RNA precipitated with 70% ethanol, washed and electrophoresed on an agarose-formaldehyde gel at 25 µg per well. Gel RNA was transferred to nitrocellulose paper, which was incubated with $^{32}$P-end labeled 40 mer cDNA probes for her-2, TGF-alpha, EGF-receptor and the MDR genes. RNA loading was comparable for all lanes as quantitated by either actin probing or by evaluation of the intensity of ribosomal-RNA bands after staining with ethidium bromide.

Results

This study was carried out to determine if the mechanism(s) of TNF-resistance conferred on MCF-7 cells by selection for resistance to doxorubicin was shared by other tissue types which were resistant to TNF de novo. Median doses for doxorubicin and TNF on MCF-7 and prostate cell lines are presented in Table 1.

TABLE 1

| Median Doses† (nM) for Doxorubicin or TNF on MCF-7 and Prostate Cells | | |
|---|---|---|
| Cell Type | Doxorubicin | TNF |
| WT | 8 | 0.18 |
| TR | 10 | 60 |
| 40F | 700 | R |
| PC3 | 121 | R |
| LNCaP | 62 | 0.16 |

†Median doses, expressed as nM drug, were determined by the method of Chou and Talalay. (22) n = 4. R = Toxicity too low to determine MD.

Median doses, expressed as nM drug, were determined by the method of Chou and Talalay. (22) n=4. R=Toxicity too low to determine MD.

Only the MCF-7 40F cells exhibited significant doxorubicin resistance (MD=700 nM), while the three MCF-7 cell lines exhibit varying degrees of TNF-sensitivity; WT cells were TNF-sensitive (MD=0.18 nM), TR cells showed an intermediate level of resistance (MD=60 nM), and 40F cells were almost completely resistant to TNF. The PC3 and LNCaP prostate lines, which were equally sensitive to doxorubicin, demonstrated disparate sensitivities to TNF. PC3 cells exhibited almost total resistance to TNF compared to the highly TNF-sensitive LNCaP cells (MD=0.16 nM).

In order to determine if differences in either receptor number or binding affinity might contribute to difference in TNF sensitivity among the various lines, TNF-receptor binding characteristics were measured for the breast and prostate cell lines. As presented in Table 2, Scatchard analysis revealed no significant differences among the WT, TR, 40F, or LNCaP cell lines, while the PC3 line had a 2-fold higher kD in comparison with the breast and LNCaP cell lines.

TABLE 2

| Scatchard Analysis of TNF Receptor Characteristics | | |
|---|---|---|
| Cell Type | Kd (nM) | Binding Capacity per Cell |
| WT | 0.648 | 5436 |
| TR | 0.664 | 5887 |
| 40F | 0.412 | 3389 |
| PC3 | 2.06 | 7838 |
| LNCaP | 0.614 | 7890 |

Dissociation constants (Kd) expressed in nM TNF, and binding capacity, expressed as molecules of TNF per cell, were derived with the Ligand- PC program. ( 37 )

To further evaluate the receptor status of these lines, the apparent molecular weight of their TNF-receptor was determined by cross-linking analysis. The apparent molecular weight of the TNF-receptors expressed by all of the cell lines was approximately 55 kD (data not shown). Thus, no significant receptor differences were noted which might account for the differential sensitivity to TNF exhibited by the cell lines.

We previously reported that, in contrast to the TNF-resistant 40F cells, the WT line exhibited increased TNF-binding over time, and that the WT cells produced a unique 15 kD TNF degradation product not produced by the 40F line. (19) In the present study, we compared WT and 40F lines with the TR and prostate lines to determine if a disparity in TNF binding, internalization or processing might exist for other TNF-resistant cells. The $^{125}$I-TNF binding and internalization data at 8, 24 and 48 hours are presented in FIG. 1. Results are depicted as CPM bound or internalized per $10^6$ cells. Each point represents the average of a triplicate determination (±1 SD).

Figure 1B:
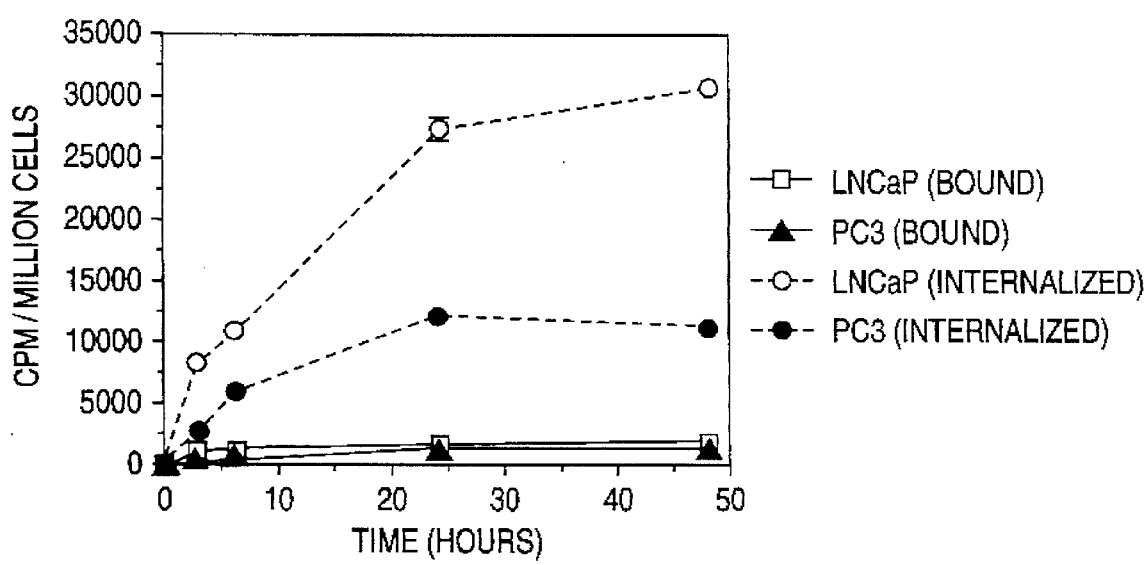

FIG. 1A indicates that the TR breast line was similar to the WT cells with respect to increased binding over time, while it was similar to the 40F line with regard to its continued uptake of TNF between 24 and 48 hours. FIG. 1B shows the binding and internalization for the prostate lines. Both the PC3 and LNCaP lines exhibited a fairly stable binding capacity over time, while internalization differed significantly, with the TNF sensitive LNCaP line taking up 2 to 3-fold more TNF than the TNF resistant PC3 line at each time point.

Figure 2A:
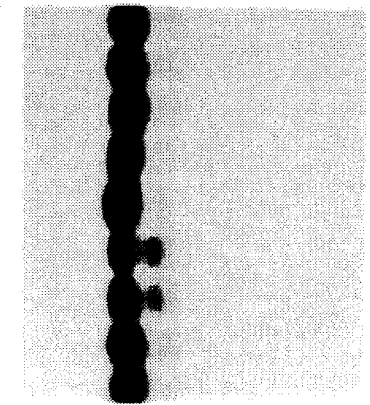
FIG. 2A shows a photocopy of SDS-PAGE of media from labeled TNF-treated cells which are either sensitive or resistant to TNF.
Figure 2B:
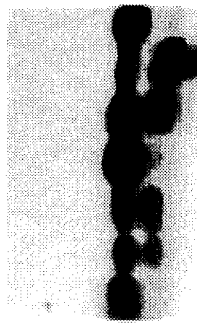
FIG. 2B shows a photocopy of SDS-PAGE of extracts of corresponding whole cells.

Electrophoretic evaluation of TNF processing by the various cell lines revealed that the WT, TR and LNCaP lines all released a 15 kD degradation product into the extracellular media (FIG. 2A). This figure shows SDS-polyacrylamide gel electrophoresis of $^{125}$I-TNF media conditioned by MCF-7 WT, 40F, TR cells, or PC3 and LNCaP prostate cells (panel A). SDS-PAGE of whole cells is also shown to depict intracellular TNF processing (panel B). Gels were run as described in the methods. TNF media control run in parallel in the absence of cells is shown in both panels. To verify that the source of the degradation products was intracellular, SDS-PAGE was done on whole cells which had been washed in glycine buffer, pH 3, to remove surface bound TNF prior to solubilization and loading onto the gel (FIG. 2B). The kinetics of product formation by the sensitive were not identical. Whereas the WT and LNCaP cells elaborated significant amounts of the 15 kD product by 24 hours, the TR cells, which are approximately 300-fold less sensitive to TNF than the WT cells, did not produce detectable amounts of the 15 kD species until 48 hours. The TNF-sensitive LNCaP cells differed somewhat from the two TNF-sensitive breast lines by producing a 13 kD product in addition to the principle 15 kD species. The 40F and PC3 TNF-resistant lines produced TNF products with multiple bands lower than 15 kD.

To determine if TNF degradation products might possess anti-tumor activity toward a TNF-resistant line, WT and LNCaP TNF-conditioned media were tested on WT and 40F cells in the absence or presence of monoclonal antibody specific for TNF. FIG. 3 shows effects of TNF-conditioned media produced by WT and LNCaP cells on WT and 40F cell line proliferation. Panel A depicts the effects of TNF, WT-CM and LNCaP-CM on WT cell proliferation in the presence (closed symbols) or absence (open symbols) of monoclonal anti-TNF-antibody (ab). Panel B depicts the effect of TNF and LNCaP-TNF-CM±ab on 40F cell proliferation. Symbol identification is indicated on the figure. Each point represents the mean of six replicates ±1 s.d. TNF concentrations for TNF-conditioned media were estimated based on the amount of TNF added to the cultures assuming no degradation or loss during concentration. Conditioned media was concentrated overnight on a Micro-ProDiCon system using PA-10 dialyais tubing.

Figure 3A:
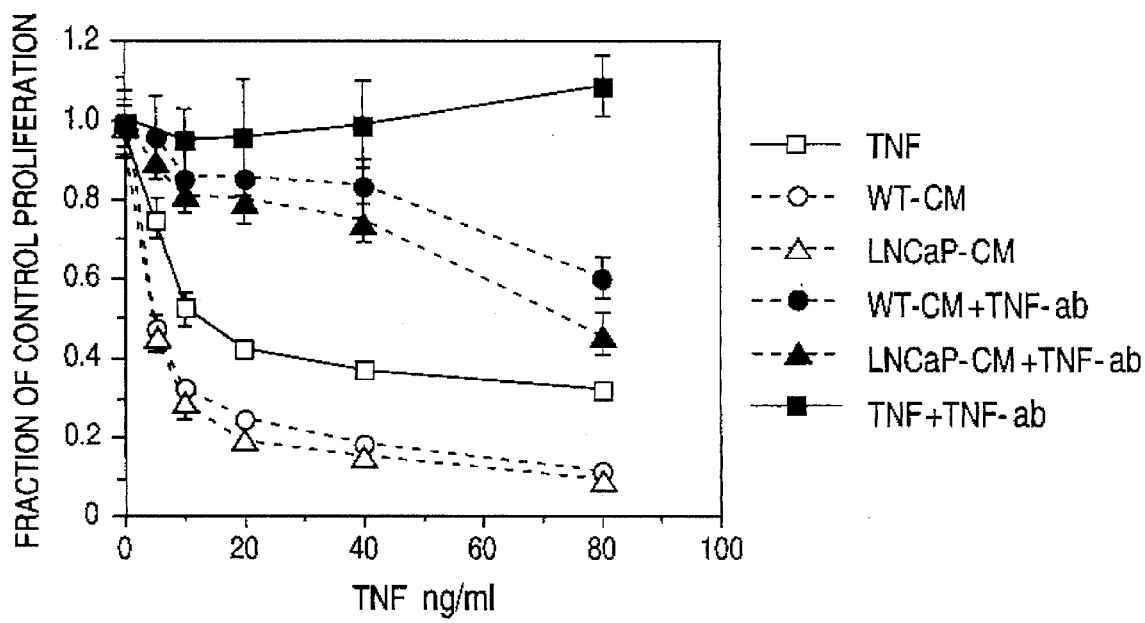
FIGS. 3A, 3B and 3C Show the effects of TNF-conditioned media produced by TNF-sensitive cells on proliferation of various tumor cell lines in the presence and absence of antibodies.
Figure 3B:
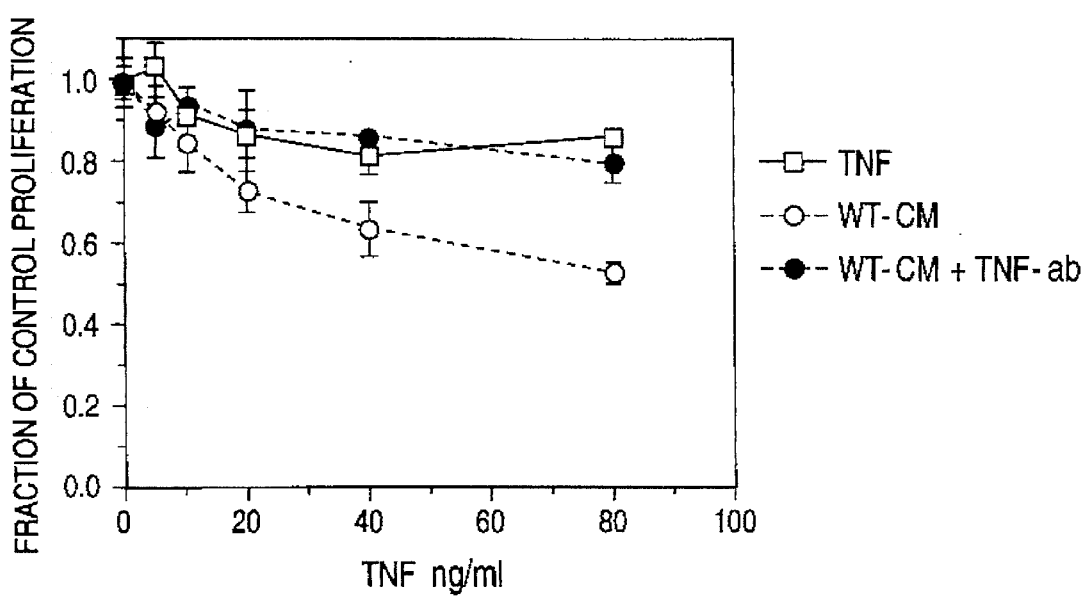
Figure 3C:
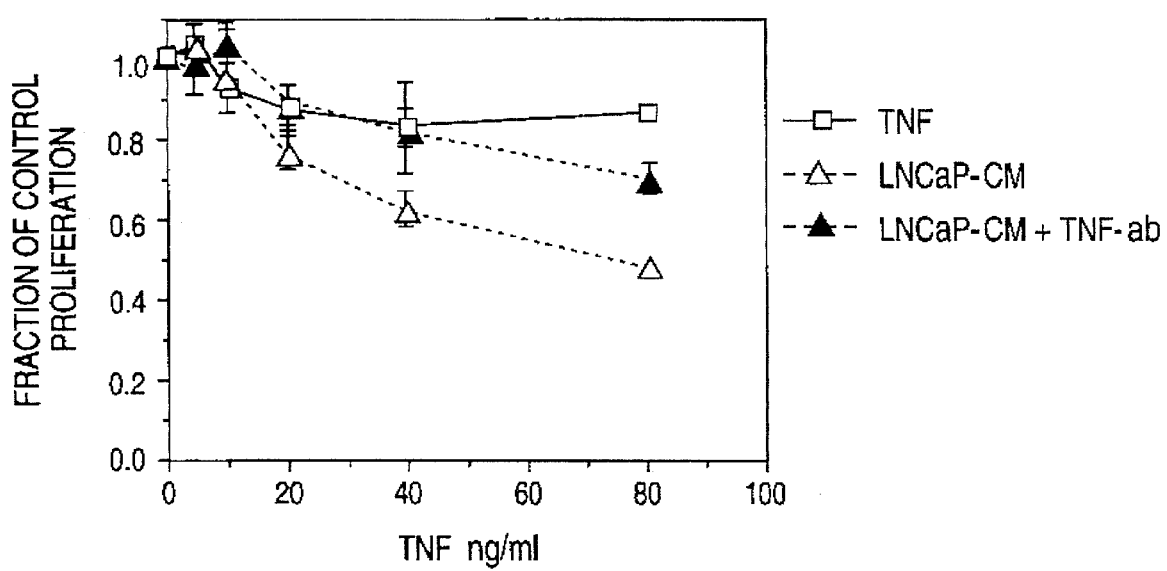

As shown in FIG. 3A, WT and LNCaP TNF-conditioned media had 2-fold greater cytotoxic activity against WT cells than did native TNF. The activity of WT- and LNCaP-CM and of native TNF was blocked by antibody toward TNF. WT and LNCaP TNF-conditioned media also had activity towards 40F cells, which was blocked by antibody (FIGS. 3B and C). It is important to note that media conditioned by WT and LNCaP cells in the absence of TNF, and tested in parallel with the TNF-conditioned media, had no inhibitory effects on cell proliferation, and that no TNF was produced by any of the cell lines., as determined by the TNF-ELISA assay (data not shown).

Figure 4A:
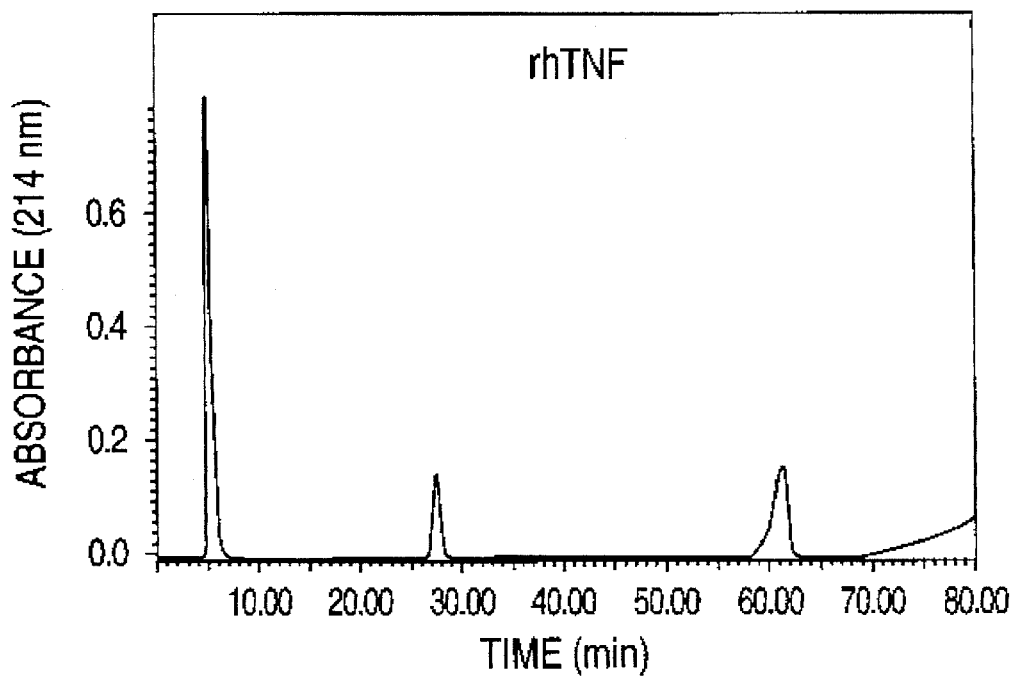
FIG. 4 (A–E) shows elution patterns from hydrophobic interaction chromatography from conditioned media of cells treated with recombinant human TNF or labeled TNF.
Figure 4B:
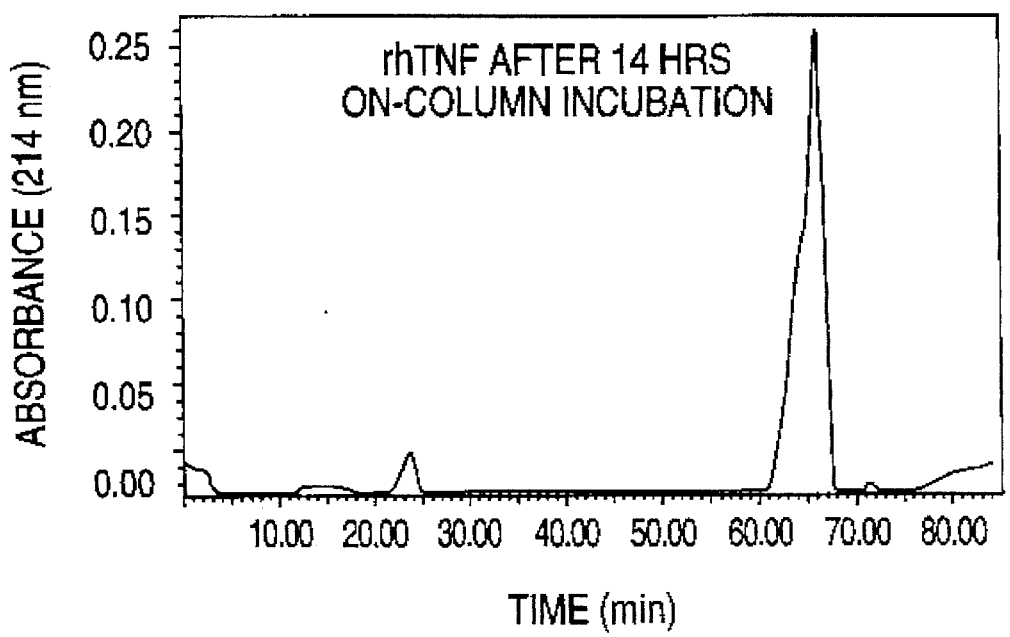
Figure 4C:
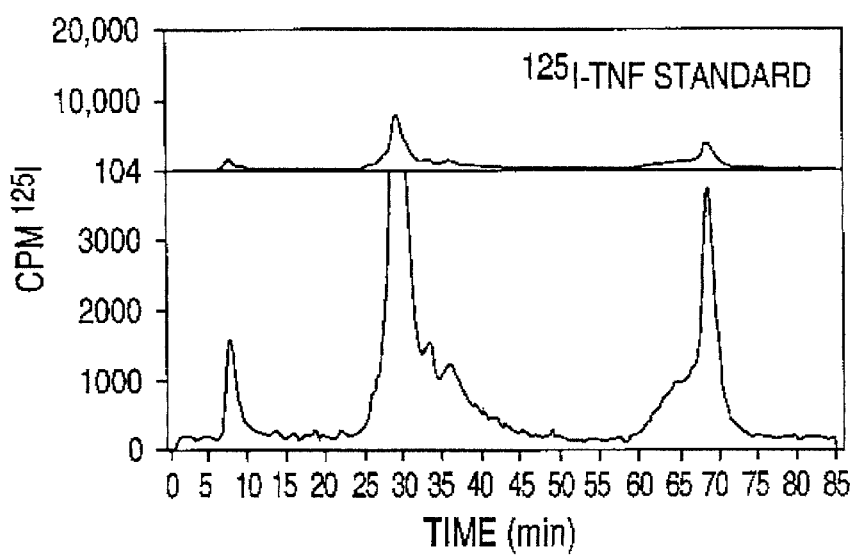

In order to further confirm that WT and LNCaP-TNF conditioned media possessed a spectrum of activity different from native TNF, we attempted to isolate the degradation products to determine if they were responsible for the antiproliferative action of conditioned media on the TNF resistant 40F cells. Hydrophobic interaction chromatography was performed to separate the different fractions of TNF. The elution profile for HIC fractionation was followed optically (214 nM) for recombinant human TNF, or with a radiomatic beta detector for $^{125}$I-TNF. FIG. 4 shows hydrophobic interaction chromatography of recombinant human tumor necrosis factor (rhTNF). Elution was followed by absorbance at 214 nm, or by CPM, versus time (minutes). Panel A depicts the elution profile of rhTNF under conditions as described in methods. Panel B shows the profile of the same quantity of rhTNF (18.7µ) after 14 hours on-column incubation. Panels C, D and E depict HIC profiles of $^{125}$I-TNF under conditions identical to rhTNF. Panel C depicts the profile for standard $^{125}$I-TNF, Panel C depicts the profile for standard $^{125}$I-TNF, Panel D for WT-$^{125}$I-TNF-CM, and Panel E for LNCaP-$^{125}$I-TNF-CM. The elution profile of rhTNF is presented in FIG. 4, Panel A. rhTNF showed trimeric, dimeric and monomeric peaks, with a short retention time (RT) for the weakly hydrophobic trimer (5.5 minutes), an intermediate RT for the dimer (27 minutes) and the longest retention time for the strongly hydrophobic monomer (61 minutes). The peak assignments are based on the shift of rhTNF peaks one and two into peak three after 14 hours on-column incubation (FIG. 4, Panel B). The equilibrium driven dissociation of the complexes into monomeric subunits during extended on-column incubation allowed for almost complete binding of the monomeric form to the column's hydrophobic phenyl groups, similar to that reported by Kunitani, et al. (21). As shown in FIG. 4B, the predominant peak after overnight incubation was the monomeric fraction. The loss of peaks at 5.5 and 27 minutes indicates that these were the trimeric and dimeric forms.

Figure 4D:
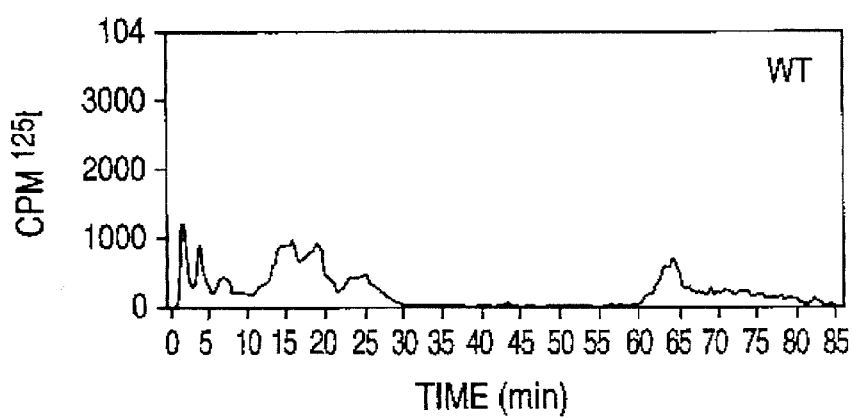
Figure 4E:
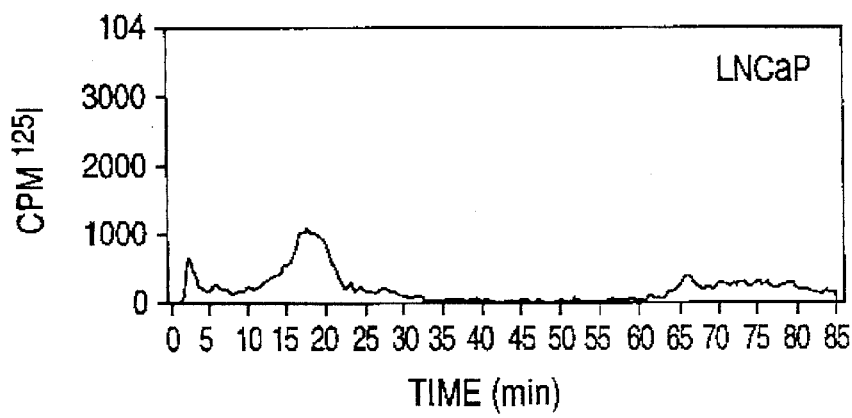
Figure 6A:
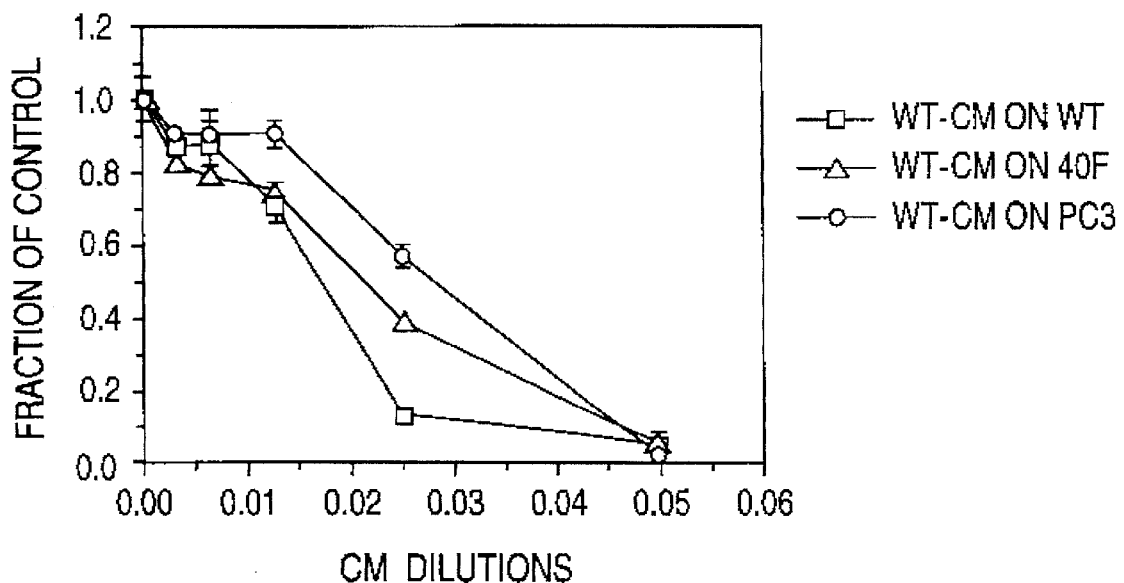
FIG. 6 (A–D) shows the results of assays of antiproliferative activity of conditioned media on various cell lines.
Figure 6B:
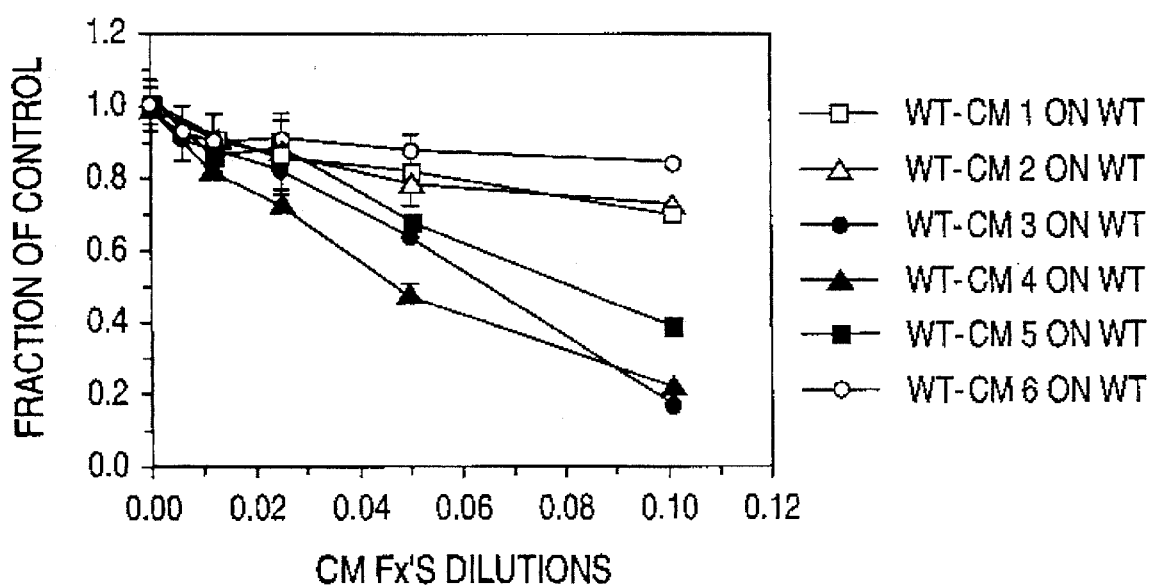
Figure 6C:
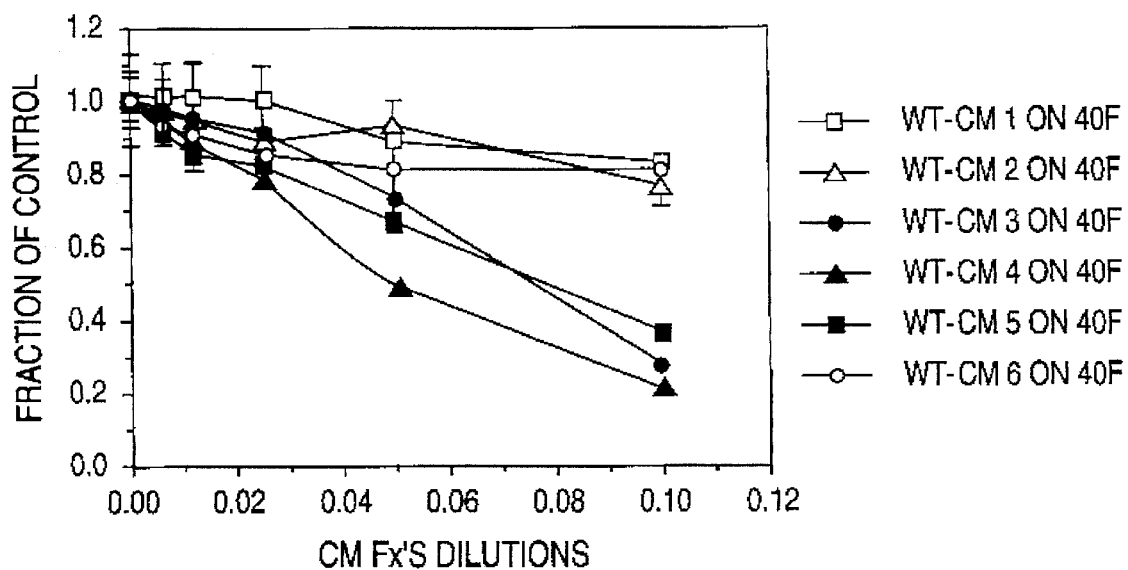
Figure 6D:
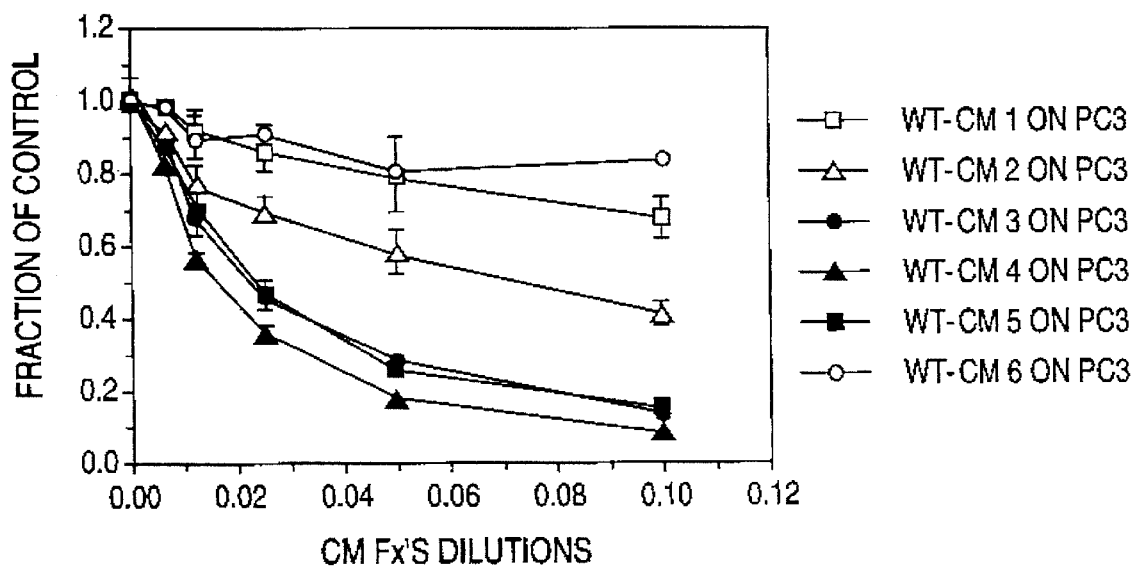

Peak elution times of radiolabeled-TNF standard, as depicted in FIG. 4D and E, were identical to those observed for rhTNF. The HIC profiles of $^{125}$-I TNF-conditioned media produced by WT cells is presented in FIG. 4D, and for LNCaP cells in FIG. 4E. Very similar peak profiles were found for the $^{125}$I-TNF-conditioned media produced by the two cell types. Fractions corresponding to the peaks were collected, concentrated and washed twice with PBS on. Centriprep-10 filtration devices, and assayed for either molecular weight composition on SDS-PAGE, or for toxicity toward the WT, 40F and PC3 cell lines in the MTT assay. Recombinant human TNF prepared in the same fashion was found to be equally active compared to unprocessed TNF (data not shown). Autoradiograms of SDS-PAGE gels run with HIC-fractions obtained from WT and LNCaP $^{125}$I-TNF-conditioned media are presented in FIG. 5, panels A and B, respectively. FIG. 5 shows SDS-PAGE autoradiograms of $^{125}$I-TNF conditioned media after HIC fractionation. Panel A represents the gel run with WT-$^{125}$I-TNF-CM, and Panel B is the gel for LNCaP-$^{125}$I-TNF-CM. Lane 1 corresponds to TNF-standard, lane 2 to unfractionated conditioned media, lane 3 to conditioned media fraction 1 (CM1) (RT=5 to 9 minutes), lane 4 to CM2 (TR=19–25), lane 5 to CM3 (RT=29–35), lane 6 to CM4 (RT=41–47), lane 7 to CM5 ( RT=60–68 ), lane 8 to CM6 ( RT=71–77 ) and lane 9 to CM7 (RT=82–88). 12.5% SDS-PAGE gel lanes were loaded with 500 cpm, and run at 30 mAmps constant current for 3 hours. Equal amounts of radioactivity were loaded into each well. Lane 1 corresponds to TNF-standard, lane 2to unfractionated conditioned media, lane 3 to conditioned media fraction 1 (CM1) (RT=5–9 minutes), lane 4 to CM2 (RT=19–25), lane 5 to CM3 (RT=29–35), lane 6 to CM4 (RT=41–47), lane 7 to CM5 (RT=60–68), lane 8 to CM6 (RT=71–77 ) and lane 9 to CM7 (RT=82–88 ). The unfractionated CM for both cell types showed the expected 17.3 and 15 kD bands. Of immediate interest was the finding that the electrophoretic profiles for the HIC fractions of $^{125}$I-TNF-conditioned media produced by the two cell types:were nearly identical. Lane 3, corresponding to the trimeric retention time, migrated on the gel as a TNF monomer, consistent with dissociation of the trimer during SDS-PAGE. CM2 was collected from a novel HIC elution peak which appeared after cellular conditioning of $^{125}$I-TNF. Although quite faint, a band at 17.3 kD was discernable, with no other detectable banding. CM3, the fraction obtained at the dimeric RT, showed a discrete band corresponding to an apparent MW of 17.3 kD. CM4 is of particular interest in that it was obtained from an elution fraction intermediate between the dimer and monomer retention times, and which exhibited a very low CPM signal. This novel fraction contained three distinct bands; 17.3 kD, 15 kD and 5.5 kD, with the 5.5 kD species predominating. This unique pattern was seen for both WT and LNCaP cells. Banding for CM5, corresponding to the monomeric RT, was fairly discrete for the WT cells, with the predominant band at 17.3 kD, while the LNCaP cells showed a predominant band at 17.3 kD, with additional band at 15 kD. The remaining two fractions, CM6 and CM7, both showed 15 kD bands, with less pronounced banding at 17.3 kD.

FIG. 6 illustrates the antiproliferative activity of WT TNF-conditioned media on WT, 40F and PC3 cells. FIG. 6 shows an MTT assay of antiproliferative activity of dilutions of WT-$^{125}$I-TNF-conditioned media on WT, 40F and PC3 cells. FIG. 6, Panel A depicts the activity of WT-$^{125}$I-TNF-CM prior to HIC fractionation. FIGS. 6B, C and D illustrate the activity of HIC fractions of WT-$^{125}$I-TNF-CM on WT, 40F and PC3 cells, respectively. Points represent triplicate determinations from a representative experiment, ±1 sd. FIG. 6A illustrates the activity of the unfractionated CM, while 6B, 6C and 6D show the antiproliferative activity of dilutions of the CM-fractions toward the WT, 40F and PC3 cell lines, respectively. The toxicity profiles of the degradation products indicated that the most potent fractions from WT cells were CM3, CM5, and CM4, corresponding to the dimeric and monomeric fractions and to the sole fraction containing the 5.5 kD degradation species (CM4). An exact potency of the fractions could not be directly determined because of the potential for contaminating protein in the fractions, and because of the potential disruption of the epitope toward which the anti-TNF monoclonal antibody employed in the ELISA is directed. Although ELISA analysis indicated that the active fractions did contain immunoreactive TNF, there was no direct correlation between the amount of TNF detected in the fractions and the antiproliferative activity (Table 3).

TABLE 3

TNF in Conditioned Media, HIC-Fractions, and Comparative Toxicities on MCF-7 40F Cells

| | WT | | LNCaP TNF @ | |
|---|---|---|---|---|
| Fx | TNF @ 1:20 dil. (pg/ml)* | Fx Inh.† MCF-7 40F | 1:20 dil (pg/ml)* | Fx Inh.† MCF-7 40F |
| CM | 88.7 ± 4.5 | 0.95 | 51.0 ± 3.0 | 0.23 |
| 1 | 1.8 ± 0.2 | 0.11 | 0.6 ± 0.2 | 0.28 |
| 2 | 2.2 + 0.3 | 0.06 | 0.6 ± 0.2 | 0.10 |
| 3 | 9.9 + 0.8 | 0.28 | 4.5 ± 0.4 | 0.16 |
| 4 | 0.9 + 0.2 | 0.51 | 0.5 ± 0.2 | 0.26 |
| 5 | 3.5 + 0.3 | 0.32 | 1.3 ± 0.2 | 0.44 |
| 6 | <0.5 | 0.19 | 0.7 ± 0.2 | 0.11 |
| 7 | <0.5 | 0.13 | <0.5 | 0.13 |

*ELISA assay of TNF content of CM and CM-fractions performed according to NEN method, with results reported as concentration of TNF in pg/ml ± S.E.M. at a 1:20 dilution of CM and fractions.
†Fraction of inhibition of MCF-7 40F breast cancer cell line proliferation compared to untreated control after treatment with a 1:20 dilution of CM or CM fractions in the MTT assay as described in methods.

The inhibitory activity of the fractions far exceeded the potential inhibition by native TNF, which had a median dose of approximately 3 ng/ml. As shown in Table 3, the most active WT TNF-CM fraction, fraction 4, showed 51% inhibition of MCF-7 40F cells at a 1:20 dilution. The TNF level at this dilution for this fraction was 0.9 pg/ml, more than 1000-fold less than the MD for TNF on TNF-sensitive MCF-7 WT cells. Table 3 also illustrates the activity of the LNCaP-CM and fractions against the 40F cell line. A relatively lower cytotoxic activity of the LNCaP-$^{125}$I-TNF-CM was noted in this experiment in comparison with the WT-$^{125}$I-TNF-CM, and the LNCaP-TNF-CM made with unlabeled TNF. This may have been due to differences in collection efficiency, and concentration methodology. Despite the relative differences in the WT and LNCaP inhibitory activity, the predominantly active CM fractions for both cell types were fractions 4 and 5.

Figure 7:
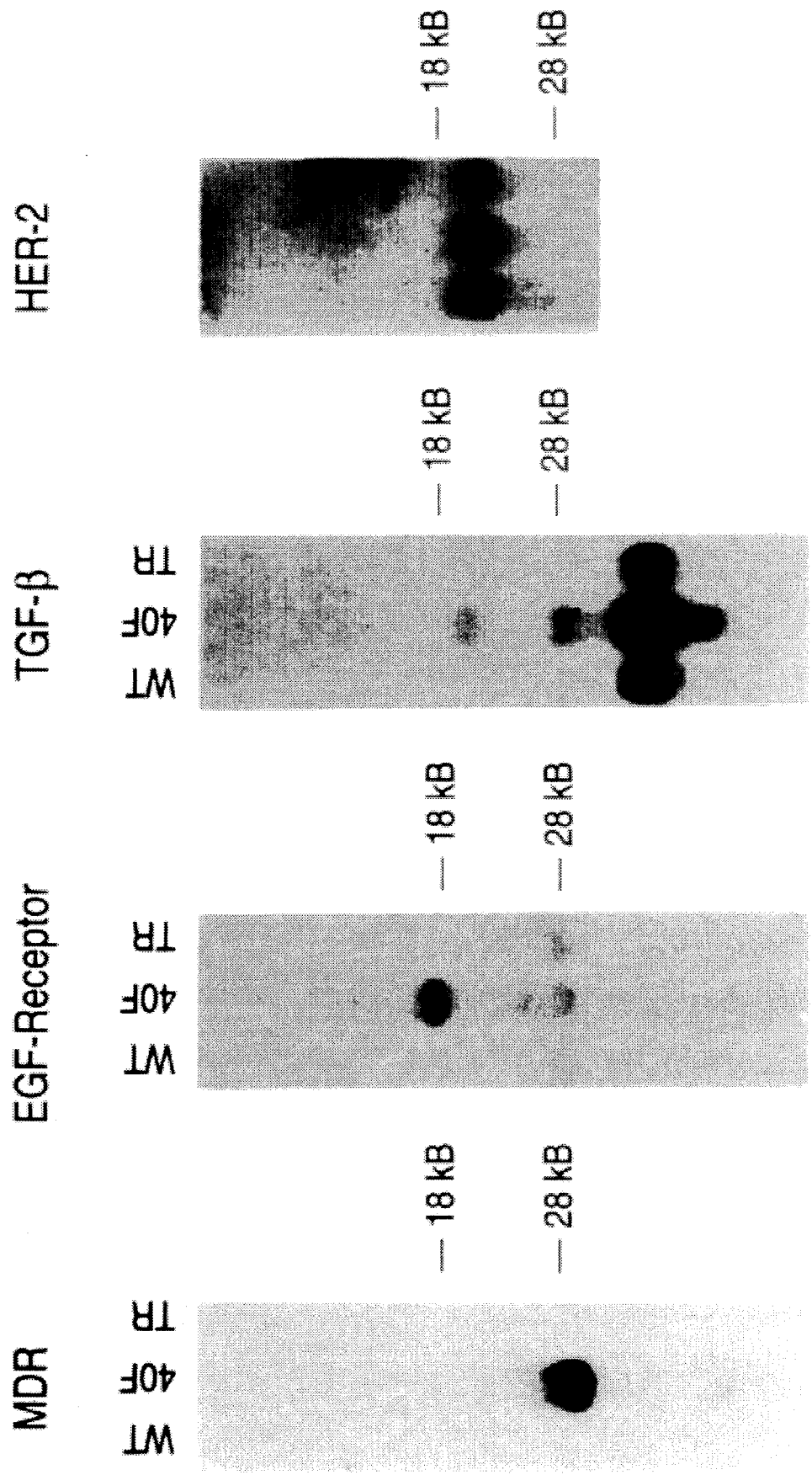
FIG. 7 is a photocopy of a Northern blot of tumor cells probed for MDR, TGF-β, EGF receptor, and her-2/neu mRNA.

To determine if there were differences in growth factor expression by the TNF-resistant and -sensitive MCF-7 cell lines, we performed Northern analysis of the breast cancer cell lines for c-erbB2/neu, TGF-beta, EGF-receptor mRNA, as well as for MDR expression. FIG. 7 shows Northern Blot analysis of MCF-7 WT, 40F and TR cells probed for MDR, TGF-beta, EGF-receptor and hero-2/neu mRNA performed as described in methods. FIG. 7 indicates that all three cell lines expressed moderate levels of c-erbB-2/neu, and moderate levels of TGF-beta, while only the MCF-7 40F line overexpressed EGF-receptor and MDR mRNA.

Thus, both the breast and prostate cell lines sensitive to TNF were found to selectively degrade internalized TNF to 15 kD and 5.5 kD products, whereas TNF resistant lines of both tissue types degraded TNF non-specifically into several molecular weights species below 15 kD. Association of cytotoxic activity was shown with the WT-CM-fraction composed primarily of the 5.5 kD species. No toxicity was shown by the last two fractions, which were primarily composed of the 15 kD fragment. Dimeric and monomeric fractions, which appeared to be composed solely of TNF monomer on the autoradiograms, showed cytotoxic activity toward TNF-resistant cells. This suggests that either other fragments may have been produced which failed to appear on the autoradiogram due to a lack of iodinated tyrosine residues, or that the activity profile of the monomer was altered without an appreciable change in its apparent molecular weight. The 5.5 kD species appeared only after HIC separation and concentration with the Centriprep-10 device, which suggests that the 5.5 kD species was probably in dimeric or trimeric association with other TNF species, and only released when exposed to the hydrophobic environment of the HIC column. Additionally, it was conserved on the Centriprep-10 filter. The Centriprep technical specifications indicate that species lower than 10 kD can be collected, but with lower efficiency. It is therefore possible that a portion of the 5.5 kD species was lost during the concentration and washing procedure.

Our observation that TNF processing differed between TNF-sensitive and TNF-resistant cells is consistent with the report of Ohsawa and Natori (supra), who found that TNF-conditioned media from L929 cells, and the L929 cell themselves, contained a discrete TNF-degradation product not produced by TNF-resistant B16 cells. This work indicates that selective intracellular TNF-processing by TNF-sensitive cells leads to the production of a cytotoxic TNF species. The MCF-7 TR cell line exhibited altered product formation kinetics, with a 24 hour delay in production of the 15 kD species compared to the fully sensitive parent line. However, no nonspecific degradation products were formed and its intermediate resistance to TNF may be due to slower activation of TNF into the active species.

With respect to the possibility that differential TNF-sensitivity and processing among the cell lines we evaluated could be due to differences in receptor expression, we failed to find any major differences in receptor number, binding affinity or molecular weight. Based on the absence of detectable TNF in media conditioned by untreated cell lines, and the comparable TNF binding characteristics of the resistant cells compared to the sensitive cells, it is unlikely that the TNF-resistant cell lines were resistant by virtue of TNF production and autodownregulation of their TNF receptors, as has been reported for ZR-75 cells by Spriggs, et al., *Proc Nat Acad Sci USA* (1987) 84:6563–6566.

Thus, differences in the degradation pathway between TNF-sensitive and -resistant cells are most likely due to differential post-receptor processing events. One potential, explanation for altered processing may relate to differences in receptor phosphorylation. Although no studies have yet reported on whether or not the TNF-receptor is phosphorylated, amino acid sequence data obtained from the cloned 55 kD TNF-receptor indicates that the cytoplasmic portion of the receptor contains motifs which could act as substrates for tyrosine kinase, protein kinase C and nucleotide dependent kinases. (25,26) Sequence homology analysis indicates that the 55 kD TNF-receptor belongs to the NGF/EGF/LDL receptor family. (25,26) Growth factor dependent tyrosine kinases are likely candidates based on reports that TNF sensitivity can be antagonized by TGF-beta, TGF-alpha, and EGF. (27) TNF sensitivity is decreased in cell lines which overexpress her-2/neu, while antibodies directed toward $p185^{HER2}$ can sensitize cells to TNF. (28,29) The cloned 55 kD TNF-receptor shares sequence homology with the EGF receptor, and the EGF-receptor-ligand complex either to the lysosome or back to the plasma membrane is regulated by receptor phosphorylation. (30) Based on this, and the finding that early actions of TNF and EGF may involve similar pathways (31), it is possible that the controls regulating the trafficking of the EGF-receptor may provide a model for TNF-receptor trafficking.

While cell lines we evaluated appeared to express comparable levels of her-2/neu mRNA, we found increased mRNA expression for TGF-beta and for the EGF-receptor by the TNF-resistant 40F cell line compared to the WT line. Altered onc gene expression may produce an autocrine loop phenotype whereby growth factors produced by the TNF-resistant cells stimulate their own EGF-receptor tyrosine kinase, which then constitutively phosphorylates the TNF receptor. TNF-receptor phosphorylation might in turn inhibit dissociation of TNF from the receptor, thereby directing the receptor-ligand complex into the lysosome for detoxification. Our finding of decreased surface binding over time by the 40F cells, compared to the increased surface binding over time by the WT cells, is consistent with receptor recycling in the WT cells, but not in the 40F cells. MCF-7 WT receptor recycling has been previously reported. (32,33) A relationship between TNF-resistance and the autocrine-loop phenotype is consistent with reports that both the MCF-7 WT and LNCaP cells are hormonally dependent, while MCF-7 doxorubicin resistant cells and PC3 cells are hormonally independent. (34–36)

Irrespective of the mechanism of differential intracellular TNF-processing, the anti-tumor activity of the CM fractions produced by both the TNF-sensitive breast and prostate lines is of particular interest. Although much speculation exists regarding the effect of TNF on phospholipase A2, endonuclease activation, and on the cells redox status, to date the mechanism of anti-tumor action has not been definitely characterized.

References

1. Selby, P.; Hobbs, S.; Viner, C. Tumor necrosis factor in man: Clinical and biological observations. Br. J. Cancer 56:803–808; 1987.
2. Spriggs, D. R.; Sherman, M. L.; Michie, H.; Arthur, K. A.; Imamura, K.; Wilmore, D.; Frei, E. III; Kufe, D. W. Recombinant human tumor necrosis factor administered as a 24-hour intravenous infusion. A phase I and pharmacologic study. J. Nat. Cancer Inst. 80:1039–1044; 1988.
3. Abbruzzese, J. L.; Levin, B.; Ajani, J. A.; Faintuch, J. S.; Saks, S.; Patt, Y. Z.; Edwards, C.; Ende, K.; Gutterman, J. U. Phase I trial of recombinant human γ-interferon and recombinant human tumor necrosis factor in patients with advanced gastrointestinal cancer. Cancer Res. 49:4057–4061; 1989.
4. Dollbaum, C.; Creasey, A. A.; Dairkee, S. H.; Hiller, A. J.; Rudolph, A. R.; Lin, L.; Vitt, C.; Smith, H. S. Specificity of tumor necrosis factor toxicity for human mammary carcinomas relative to normal mammary epithelium and correlation with response to doxorubicin. Proc. Nat. Aced. Sci. 85: 4740–4744; 1988.
5. Hofsli, E.; Nissen-Meyer, J. Effect of erythromycin and tumor necrosis factor on the drug resistance of multidrug-resistant cells: Reversal of drug resistance by erythromycin. Int. J. Cancer 43:520–525; 1989.
6. Shepard, H. M.; Lewis, G. D. Resistance of tumor cells to tumor necrosis factor. J. Clin. Immunol. 8:333–341; 1988.
7. Smith, R. A.; Baglioni, C. The active form of tumor necrosis factor is a trimer. J. Biol. Chem. 262:6951–6956; 1987.
8. Mosselmans, R.; Hepburn, A.; Dumont, J. E.; Fiers, W.; Garland, P. Endocytic pathway of recombinant murine tumor necrosis factor in L929 cells. J. Immunol. 141:3096–3100; 1988.
9. Tsujimoto, M.; Yip, Y. K.; Vilcek, J. Tumor necrosis factor: Specific binding and internalization in sensitive and resistant cells. Proc. Nat. Acad. Sci. (USA) 82:7626–7630; 1985.
10. Kull, F. C. Jr.; Cuatrecasas, P. Possible requirement of internalization in the mechanism of in vitro cytotoxicity in tumor necrosis factor serum. Cancer Res. 41:4885–4890; 1988.
11. Vilcek, J.; Lee, T. H. Tumor necrosis factor: New insights into the molecular mechanisms of its multiple actions. J. Biol. Chem. 266: 7313–7316; 1991.
12. Larrick, J. W.; Wright, S. C. Cytotoxic mechanism of tumor necrosis factor-αFASEB J. 4:3215–3223; 1990.
13. Jäättela, M. Biologic activities and mechanism of action of tumor necrosis factor-α/cachectin. Lab. Invest. 64:724–742; 1991.
14. Watanabe, N.; Yoshiro, N.; Neda, H.; Sone, H.; Yamauchi, N.; Maeda, M.; Urushizaki, I. Cytocidal mechanisms of TNF: Effects of lysosomal enzyme and hydroxyl radical inhibitors on cytotoxicity. Immunopharm. Immunotox. 10: 109–196; 1988.
15. Aggarwal, B. B.; Traquina, P. R.; Eessalu, T. E. Modulation of receptors and cytotoxic response of tumor necrosis factor-a by various lectins. J. Biol. Chem. 261:13652–13656; 1986.
16. Liddil, J. D.; Dorr, R. T.; Scuderi, P. Association of lysosomal activity with sensitivity and resistance to tumor necrosis factor in murine L929 cells. Cancer Res. 49:2717–2718; 1989.
17. Kull, F. C.; Besterman, J. M. Drug-induced alterations of tumor necrosis factor-mediated cytotoxicity: discrimination of early versus late stage action. J. Cell. Biochem. 42:1–9; 1990.
18. Ohsawa, F.; Natori, S. Selective degradation of tumor necrosis factor in sensitive cells, and production of membrane active substance. J. Biochem. 103:730–734; 1988.
19. Fruehauf, J. P.; Mimnaugh, E. G.; Sinha BK. Doxorubicin-induced cross-resistance to tumor necrosis factor (TNF) related to differential TNF processing. J. Immunotherapy 10:165–173; 1991.
20. Fruehauf, J. P.; Myers, C. E.; Sinha, B. K. Synergistic activity of suramin with tumor necrosis factor-αand doxorubicin on human prostate cancer cell lines. J. Nat. Cancer Inst. 82:1206–1209; 1990.
21. Kunitani, M. G.; Cunico, R. L.; Staats, S. J. Reversible subunit dissociation of tumor necrosis factor during hydrophobic interaction chromatography. J. Chromatog. 443:205–220; 1988.
22. Chou, T. C.; Talalay, P. Quantitative analysis of dose-effect relationships: The combined effects of multiple drugs or enzyme inhibitors. In: Weber, G., ed. Advances in enzyme regulation, Vol. 22. Oxford: Pergamon Press; 1983: pp. 27–55.
23. Horuk, R. Differences in internalization and intracellular processing of interleukin-1 associated with two forms of interleukin-1 receptor found in B-cells and T-cells. Biochem. J.273:79–83; 1991.
24. Spriggs, D.; Imamura, K.; Rodriguez, C.; Horiguchi, J.; Kufe, D. W. Induction of tumor necrosis factor expression and resistance in a human breast tumor cell line. Proc. Nat. Acad. Sci. USA 84;6563–6566; 1987

25. Schall, T. J.; Lewis, M.; Koller, K. J.; Lee, A.; Rice, GC; Wong, G. H. W.; Gatanaga, T.; Granger, G. A.; Lentz, R.;Raab, H.; Kohr, W. J.; Goeddel, D. V. Molecular cloning and expression of a receptor for human tumor necrosis factor. Cell 61:361–370; 1990.

26. Loetscher, H.; Pan, Y. E.; Lahm, H.; Gentz, R.; Brockhaus, M.; Tabuchi, H.; Lesslauer, W. Molecular cloning and expression of the human 55 kd tumor necrosis factor receptor. Cell 61:351–359;1990.

27. Sugarman, B. J.; Lewis, G. D.; Eessalu, T. E.; Aggarwal, B. B.; Shepard, H. M. Effects of growth factors on the antiproliferative activity of tumor necrosis factors. Cancer Res. 47:780–786; 1987.

28. Lichtenstein, A.; Berenson, J.; Gera, J. F., Waldburger, K.; Martinez-Maz, O.; Berek, J. S. Resistance of human ovarian cancer cells to tumor necrosis factor and lymphokine-activated killer cells: Correlation with expression of HER2/neu oncogenes. Cancer Res. 50:7364–7370; 1990.

29. Hudziak, R. M.; Lewis, G. D.; Winget, M.; Fendly, B. M.; Shepard, H. M.; Ullrich, A. p185$^{HER2}$ Monoclonal antibody has antiproliferative effects in vitro and sensitizes human breast tumor cells to tumor necrosis factor. Mol. and Cellular Biol. 9:1165–1172; 1989.

30. Decker, S. J. Epidermal growth factor and transforming growth factor-alpha induce differential processing of epidermal growth factor receptor. Biochem. Biophys. Res. Comm. 166:615–621; 1990.

31. Donato, N.; Ince, C.; Rosenblum, M. G.; Gallick, G. E. Early events in the antiproliferative action of tumor necrosis factor are similar to the early events in epidermal growth factor growth stimulation, J. Cell. Biochem. 41:139–157; 1989.

32. Bajzer, Z.; Myers, A. C.; Vuk-Pavlovic, S. Binding, internalization and intracellular processing of proteins interacting with recycling receptors. J. Biol. Chem. 264:13623–13631; 1989.

33. Vuk-Pavlovic, S.; Kovach, J. S. Recycling of tumor necrosis factor-alpha receptor in MCF-7 cells. FASEB J. 3:2633–2640; 1989.

34. Vickers, P. J.; Dickson, R. B.; Shoemaker, R.; Cowan, K. H. A multidrug-resistant MCF7 human breast cancer cell line which exhibits cross-resistance to antiestrogens and hormone-independent tumor growth in vivo. Mol. Endo. 2:886–892; 1988.

35. Kaighn, M. E.; Narayan, K. S.; Ohnuki, Y; Lechner, J. F.; Jones, L. W. Establishment and characterization of a human prostatic carcinoma cell line (PC-3). Inv. Urol. 17:16–23; 1979.

36. Horoszewicz, J. S., Leon, S. S.; Kawinski, E.; Karr, J. P.; Rosenthal, H.; Chu, T. M.; Mirand, E. A., Murphy, G. P. LNCaP model of human prostatic carcinoma. Cancer Res. 43:1809–1818; 1983.

37. Munson, P. J.;Rodbard, D. LIGAND; a versitile computerized approach for characterization of ligand-binding systems. Anal. Biochem. 107:220–239; 1980.

I claim:

1. A substantially purified and isolated 5.5 kD degradation product of TNF or multimers of TNF, said product being obtained by hydrophobic interaction chromatography of TNF-conditioned media from TNF-sensitive cells.

2. A pharmaceutical composition comprising an effective tumor-cytotoxic amount of a substantially purified 5.5 kD degradation product of TNF or multimers of TNF, said product being obtained by hydrophobic interaction chromatography of TNF-conditioned media from TNF-sensitive cells and a pharmaceutically acceptable carrier.

* * * * *